United States Patent
Hirano et al.

(10) Patent No.: US 7,867,735 B2
(45) Date of Patent: Jan. 11, 2011

(54) L-GLUTAMIC ACID PRODUCING BACTERIUM AND A METHOD FOR PRODUCTION OF L-GLUTAMIC ACID

(75) Inventors: Seiko Hirano, Kawasaki (JP); Jun Nakamura, Kawasaki (JP); Hisao Ito, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 199 days.

(21) Appl. No.: 12/034,101

(22) Filed: Feb. 20, 2008

(65) Prior Publication Data

US 2009/0258402 A1    Oct. 15, 2009

Related U.S. Application Data

(63) Continuation of application No. PCT/JP2006/317036, filed on Aug. 23, 2006.

(30) Foreign Application Priority Data

Aug. 26, 2005    (JP) .............................. 2005-245214

(51) Int. Cl.
*C12P 21/00* (2006.01)
*C12N 1/20* (2006.01)

(52) U.S. Cl. ................... 435/70.1; 435/71.1; 435/252.1

(58) Field of Classification Search ........................ None
See application file for complete search history.

(56) References Cited

U.S. PATENT DOCUMENTS 5,846,790 A    12/1998    Kimura et al.
2005/0153402 A1    7/2005    Pompejus et al.

FOREIGN PATENT DOCUMENTS

| DE | 101 28 510 | 12/2002 |
| EP | 0 469 517 | 2/1992 |
| EP | 1 108 790 | 6/2001 |
| WO | WO96/06180 | 2/1996 |

OTHER PUBLICATIONS

Kimura, E., et al., "Metabolic Engineering of Glutamate Production," Advances in Biochem. Eng. 2003;79:37-57.
Supplementary European Search Report for EP Patent App. No. 06797011.1 (Oct. 16, 2009).
Kawahara, Y., et al., "Relationship between the Glutamate Production and the Activity f2-Oxoglutarate Dehydrogenase in *Brevibacterium lactofermentum*," Biosci. Biotech. Biochem. 1997;61(7):1109-1112.
Kimura, E., et al., "A *dtsR* Gene-Disrupted Mutant of *Brevibacterium lactofermentum* Requires Fatty Acids for Growth and Efficiently Produces L-Glutamate in the Presence of an Excess of Biotin," Biochem. Biophys. Res. Comm. 1997;234:157-161.
International Preliminary Report on Patentability for PCT/JP2006/317036 dated Sep. 18, 2006.

*Primary Examiner*—James (Doug) Schultz
(74) *Attorney, Agent, or Firm*—Shelly Guest Cermak; Cermak Nakajima LLP

(57) ABSTRACT

A method for producing L-glutamic acid by culturing a coryneform bacterium which has L-glutamic acid producing ability and which has been modified so that expression of the fasR gene is enhanced in a medium to produce and accumulate L-glutamic acid in the medium or cells, and collecting L-glutamic acid from the medium or cells.

3 Claims, 2 Drawing Sheets

SEQUENCE LISTING

```
<160> NUMBER OF SEQ ID NOS: 6

<210> SEQ ID NO 1
<211> LENGTH: 40
<212> TYPE: DNA
<213> ORGANISM: Artificial
<220> FEATURE:
<223> OTHER INFORMATION: primer for amplifying fasR

<400> SEQUENCE: 1
gccgggtacc gctgccacaa atcgggcaag gataatctgc                40

<210> SEQ ID NO 2
<211> LENGTH: 40
<212> TYPE: DNA
<213> ORGANISM: Artificial
<220> FEATURE:
<223> OTHER INFORMATION: primer for amplifying fasR

<400> SEQUENCE: 2
gccgggtacc tcaaattccg gagttgagat ggagaaaact                40

<210> SEQ ID NO 3
<211> LENGTH: 1020
<212> TYPE: DNA
<213> ORGANISM: Corynebacterium glutamicum
<220> FEATURE:
<221> NAME/KEY: CDS
<222> LOCATION: (506)..(976)
<223> OTHER INFORMATION: fasR

<400> SEQUENCE: 3
gcctgccgtc cattctttac caactgttcg atttcttctt cacttcgagc agaacctgcc    60
gcccgaccga tttcatcgcc ataaacccac aaaaccacac gtagatcctc gctgccacaa   120
```

```
atcgggcaag dataatctgc gaggtgtccg tgatatttgc tcgcagtcac caagatgaac      180
tcggcgtcac aaattgtgtc tttttgcacc aaccccgccc gaaactgacg gagagtctgc      240
ctacgagcta gttggtgact gatctcattt tgatattgca ccacgattaa aaagtgtagc      300
cgtaagccga ccaatgaaac gaccctctag aagcatcgtt tagaattgct tttaagtgaa      360
taaggaacag cacagaatta aggcgtcgga gttatcgctc acgctacttc tcaagtggcg      420
ccaaggtaag ttgtactttt tctgtccaaa ttattgtttt ttccgtagat aggttatcga      480
acggaaatta cttggcaata ccgct atg ctg gca ggc atg cct aat tta aac        532
                             Met Leu Ala Gly Met Pro Asn Leu Asn
                               1               5 gct gag gag cta gca gtc cgc gtg cga ccc gcg ctg aca aaa ctc tac        580
Ala Glu Glu Leu Ala Val Arg Val Arg Pro Ala Leu Thr Lys Leu Tyr
 10              15                  20                  25 gtt ctc tat ttc cgc cgc tct gtg aat tct gac ctc tcg ggt cca cag        628
Val Leu Tyr Phe Arg Arg Ser Val Asn Ser Asp Leu Ser Gly Pro Gln
             30                  35                  40 ctc act att ttg agt cgc ctg gaa gaa aac ggc cca tcc cga att agt        676
Leu Thr Ile Leu Ser Arg Leu Glu Glu Asn Gly Pro Ser Arg Ile Ser
             45                  50                  55 cgc atc gcg gaa ctt gaa gat att cgt atg cca acc gct tcg aat gct        724
Arg Ile Ala Glu Leu Glu Asp Ile Arg Met Pro Thr Ala Ser Asn Ala
             60                  65                  70 ctg cat cag ctg gag caa ctc aac ctg gtt gag cgt atc cgc gac acc        772
Leu His Gln Leu Glu Gln Leu Asn Leu Val Glu Arg Ile Arg Asp Thr
 75                  80                  85 aaa gac cgc cga ggc gtg cag gtt cag ctc act gat cat gga cgc gaa        820
Lys Asp Arg Arg Gly Val Gln Val Gln Leu Thr Asp His Gly Arg Glu
 90                  95                 100                 105 gag ctt gag cgc gtg aac aat gaa cga aac gca gag atg gct cga ctc        868
Glu Leu Glu Arg Val Asn Asn Glu Arg Asn Ala Glu Met Ala Arg Leu
                    110                 115                 120 ctt gaa atg ctc acc cca gag cag ctg gag cgt acc gaa gac ctg gtg        916
Leu Glu Met Leu Thr Pro Glu Gln Leu Glu Arg Thr Glu Asp Leu Val
                125                 130                 135 gat atc att act gag ctt gca gag gtg tac ggt agc tgg aaa gag acc        964
Asp Ile Ile Thr Glu Leu Ala Glu Val Tyr Gly Ser Trp Lys Glu Thr
            140                 145                 150 gac agc ggt tct taacagtttt ctccatctca actccggaat tgatgaaac aacc        1020
Asp Ser Gly Ser
            155

<210> SEQ ID NO 4
<211> LENGTH: 157
<212> TYPE: PRT
<213> ORGANISM: Corynebacterium glutamicum

<400> SEQUENCE: 4

Met Leu Ala Gly Met Pro Asn Leu Asn Ala Glu Glu Leu Ala Val Arg
  1               5                  10                  15

Val Arg Pro Ala Leu Thr Lys Leu Tyr Val Leu Tyr Phe Arg Arg Ser
                 20                  25                  30

Val Asn Ser Asp Leu Ser Gly Pro Gln Leu Thr Ile Leu Ser Arg Leu
             35                  40                  45

Glu Glu Asn Gly Pro Ser Arg Ile Ser Arg Ile Ala Glu Leu Glu Asp
         50                  55                  60

Ile Arg Met Pro Thr Ala Ser Asn Ala Leu His Gln Leu Glu Gln Leu
 65                  70                  75                  80
```

```
Asn Leu Val Glu Arg Ile Arg Asp Thr Lys Asp Arg Arg Gly Val Gln
                85                  90                  95

Val Gln Leu Thr Asp His Gly Arg Glu Glu Leu Glu Arg Val Asn Asn
            100                 105                 110

Glu Arg Asn Ala Glu Met Ala Arg Leu Leu Glu Met Leu Thr Pro Glu
        115                 120                 125

Gln Leu Glu Arg Thr Glu Asp Leu Val Asp Ile Ile Thr Glu Leu Ala
    130                 135                 140

Glu Val Tyr Gly Ser Trp Lys Glu Thr Asp Ser Gly Ser
145                 150                 155

<210> SEQ ID NO 5
<211> LENGTH: 474
<212> TYPE: DNA
<213> ORGANISM: Corynebacterium glutamicum
<220> FEATURE:
<221> NAME/KEY: CDS
<222> LOCATION: (1)..(474)
<223> OTHER INFORMATION: fasR

<400> SEQUENCE: 5 atg ctg gca ggc atg cct aat tta aac gct gag gag cta gca gtc cgc      48
Met Leu Ala Gly Met Pro Asn Leu Asn Ala Glu Glu Leu Ala Val Arg
1               5                   10                  15 gtg cga ccc gcg ctg aca aaa ctc tac gtt ctc tat ttc cgc cgc tct      96
Val Arg Pro Ala Leu Thr Lys Leu Tyr Val Leu Tyr Phe Arg Arg Ser
            20                  25                  30 gtg aat tct gac ctc tcg ggt cca cag ctc act att ttg agt cgc ctg     144
Val Asn Ser Asp Leu Ser Gly Pro Gln Leu Thr Ile Leu Ser Arg Leu
        35                  40                  45 gaa gaa aac ggc cca tcc cga att agt cgc atc gcg gaa ctt gaa gat     192
Glu Glu Asn Gly Pro Ser Arg Ile Ser Arg Ile Ala Glu Leu Glu Asp
    50                  55                  60 att cgt atg cca acc gct tcg aat gct ctg cat cag ctg gag caa ctc     240
Ile Arg Met Pro Thr Ala Ser Asn Ala Leu His Gln Leu Glu Gln Leu
65                  70                  75                  80 aac ctg gtt gag cgt atc cgc gac acc aaa gac cgc cga ggc gtg cag     288
Asn Leu Val Glu Arg Ile Arg Asp Thr Lys Asp Arg Arg Gly Val Gln
                85                  90                  95 gtt cag ctc act gat cat gga cgc gaa gag ctt gag cgc gtg aac aat     336
Val Gln Leu Thr Asp His Gly Arg Glu Glu Leu Glu Arg Val Asn Asn
            100                 105                 110 gaa cga aac gca gag atg gct cga ctc ctt gaa atg ctc acc cca gag     384
Glu Arg Asn Ala Glu Met Ala Arg Leu Leu Glu Met Leu Thr Pro Glu
        115                 120                 125 cag ctg gaa cgt acc gaa gac ctg gtg gat atc att act gag ctt gca     432
Gln Leu Glu Arg Thr Glu Asp Leu Val Asp Ile Ile Thr Glu Leu Ala
    130                 135                 140 gag gtg tac ggt agc tgg aaa gag acc gac agc ggt tct taa             474
Glu Val Tyr Gly Ser Trp Lys Glu Thr Asp Ser Gly Ser
145                 150                 155

<210> SEQ ID NO 6
<211> LENGTH: 157
<212> TYPE: PRT
<213> ORGANISM: Corynebacterium glutamicum

<400> SEQUENCE: 6

Met Leu Ala Gly Met Pro Asn Leu Asn Ala Glu Glu Leu Ala Val Arg
1               5                   10                  15
```

```
                              -continued

Val Arg Pro Ala Leu Thr Lys Leu Tyr Val Leu Tyr Phe Arg Arg Ser
            20                  25                  30

Val Asn Ser Asp Leu Ser Gly Pro Gln Leu Thr Ile Leu Ser Arg Leu
            35                  40                  45

Glu Glu Asn Gly Pro Ser Arg Ile Ser Arg Ile Ala Glu Leu Glu Asp
    50                  55                  60

Ile Arg Met Pro Thr Ala Ser Asn Ala Leu His Gln Leu Glu Gln Leu
65                  70                  75                  80

Asn Leu Val Glu Arg Ile Arg Asp Thr Lys Asp Arg Arg Gly Val Gln
                85                  90                  95

Val Gln Leu Thr Asp His Gly Arg Glu Glu Leu Glu Arg Val Asn Asn
            100                 105                 110

Glu Arg Asn Ala Glu Met Ala Arg Leu Leu Glu Met Leu Thr Pro Glu
            115                 120                 125

Gln Leu Glu Arg Thr Glu Asp Leu Val Asp Ile Ile Thr Glu Leu Ala
    130                 135                 140

Glu Val Tyr Gly Ser Trp Lys Glu Thr Asp Ser Gly Ser
145                 150                 155
```

L-GLUTAMIC ACID PRODUCING BACTERIUM AND A METHOD FOR PRODUCTION OF L-GLUTAMIC ACID

This application is a continuation of PCT/JP2006/317036, filed Aug. 23, 2006. This application also claims priority under 35 U.S.C. §119 to Japanese application 2005-245214 filed on Aug. 26, 2005. Each of these documents is incorporated in their entireties by reference. The Sequence Listing in electronic format filed herewith is also hereby incorporated by reference in its entirety (File Name: US-357_Seq_List_Copy_1; File Size: 9 KB; Date Created: Feb. 20, 2008).

BACKGROUND OF THE INVENTION

1. Field of the Invention

The present invention relates to the fermentation industry, and more specifically relates to a method for producing L-glutamic acid using a coryneform bacterium. L-Glutamic acid is widely used as a raw material in seasonings.

2. Brief Description of the Related Art

L-glutamic acid is conventionally produced by fermentation using coryneform bacteria belonging to the genus *Brevibacterium*, *Corynebacterium* or the like, which are able to produce L-glutamic acid. In order to improve productivity of these coryneform bacteria, strains isolated from nature, mutant strains, or strains modified by gene recombination are typically used.

Wild-type strains of coryneform bacteria do not produce L-glutamic acid when excess biotin is present in the fermentation medium. Therefore, conventional L-glutamic acid production methods restrict the amount of biotin by adding a surfactant or lactam antibiotic, which are known biotin suppressing agents, at the beginning or throughout the culture. However, many inexpensive raw materials used as carbon sources in culturing contain an excessive amount of biotin, such as blackstrap molasses. In such a case, the necessary addition of the above-mentioned biotin suppressing agent can greatly increase the cost of production (Biosci. Biotech. Biochem., 61(7), 1109-1112, 1997).

The dtsR gene, which encodes the DTSR protein from a *Corynebacterium*, was identified and found to impart resistance to a surfactant to the bacteria. Furthermore, when this gene is disrupted in an L-glutamic acid producing coryneform bacterium, a marked amount of L-glutamic acid is produced, even when biotin is present in an amount that would be significantly inhibitory in wild-type strains. Also, when the dtsR gene is amplified in an L-glutamic acid producing coryneform bacterium, the ability of the bacterium to produce L-glutamic acid is enhanced.

Moreover, it has also been found that if temperature sensitivity to biotin suppressing agents is imparted to an L-glutamic acid producing coryneform bacterium, the bacterium can stably produce L-glutamic acid by fermentation even in the presence of biotin. Furthermore, if the ability to produce L-lysine is imparted to this stain, L-lysine and L-glutamic acid can be simultaneously produced by fermentation even in the presence of biotin. It has also been found that using a variant dtsR gene produced by gene substitution which encodes a temperature sensitive DTSR protein imparts temperature sensitivity to a biotin suppressing agent to coryneform bacteria (International Patent Publication WO96/06180).

However, a gene which improves sensitivity to a surfactant when overexpressed in coryneform bacteria has not been reported.

Non-patent document 2: Biochem. Biophys. Res. Commun., 1997 May 8, 234(1):157

Patent document 1: International Patent Publication WO95/23224

SUMMARY OF THE INVENTION

An aspect of the present invention is to provide a novel method for improving the ability of a coryneform bacterium to produce L-glutamic acid during fermentation.

The inventors of the present invention conducted various research to achieve the aforementioned aspect. As a result, it was found that by amplifying the fasR gene of coryneform bacteria, the ability of the bacteria to produce L-glutamic acid was improved. Furthermore, L-glutamic acid was able to be produced in a biotin-rich medium without having to add a biotin suppressing agent, such as a surfactant.

It is an aspect of the present invention to provide a coryneform bacterium able to produce L-glutamic acid, wherein the expression of the fasR gene is increased as compared to a coryneform bacterium in which the expression of the fasR gene is not increased, and wherein said bacterium has increased sensitivity to a surfactant as compared with a bacterium in which the expression of the fasR gene is not increased.

It is a further aspect of the present invention to provide the coryneform bacterium as described above, wherein the fasR gene is selected from the group consisting of:

(a) a DNA comprising the nucleotide sequence of 506 to 976 in SEQ ID NO: 3, (b) a DNA which is able to hybridize with the nucleotide sequence of 506 to 976 in SEQ ID NO: 3 under stringent conditions, and wherein said DNA encodes a protein with increased sensitivity to a surfactant when expression of said DNA is enhanced in the coryneform bacterium.

It is a further aspect of the present invention to provide the coryneform bacterium as described above, wherein the expression of the fasR gene is enhanced by increasing the copy number of the gene or modifying an expression control sequence of the gene.

It is a further aspect of the present invention to provide a method for producing L-glutamic acid comprising:

A) culturing the coryneform bacterium as described above in a medium, and

B) collecting L-glutamic acid from the medium or the bacterium.

DESCRIPTION OF THE PREFERRED EMBODIMENTS

Figure 1:
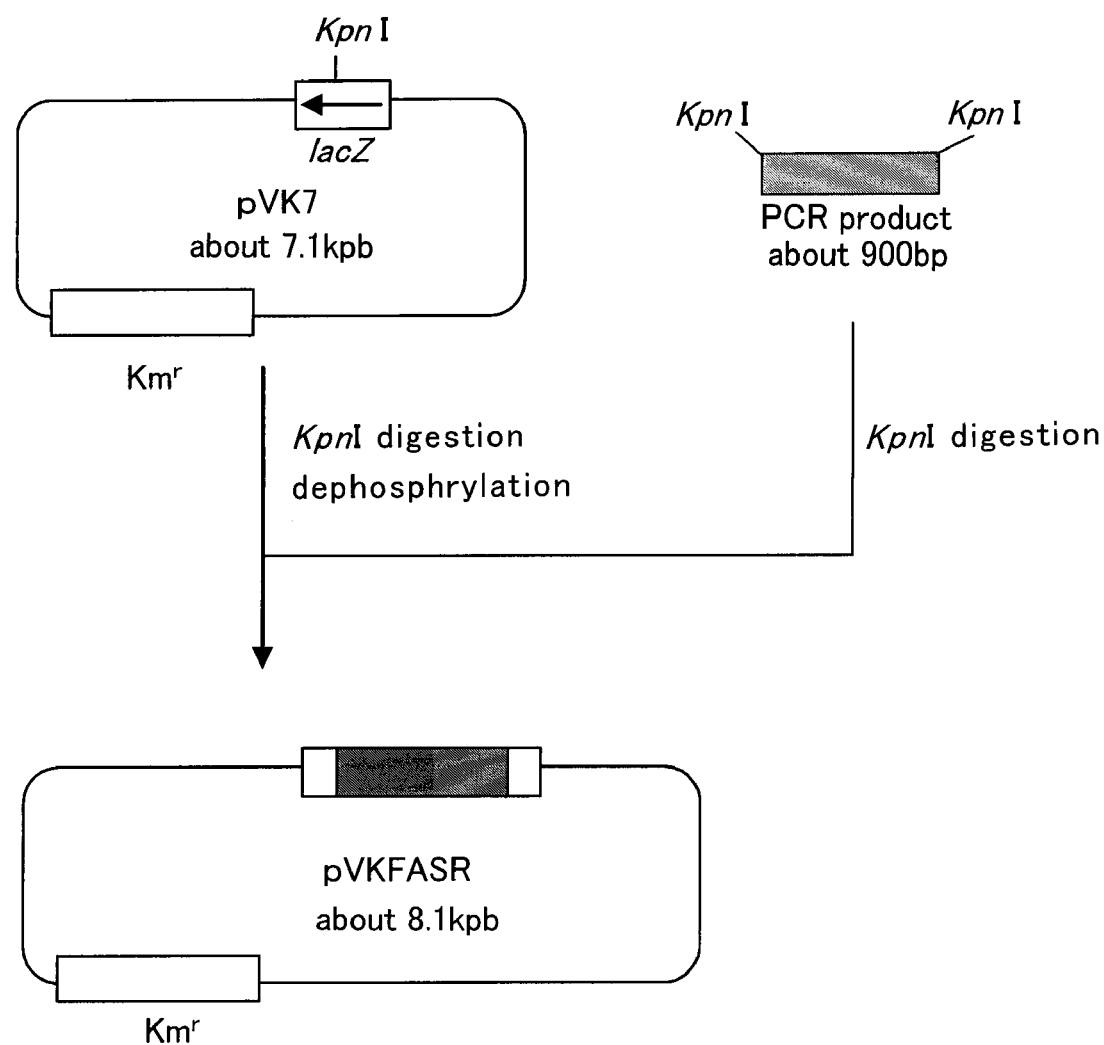
FIG. 1 shows the construction procedure of the plasmid pVKFASR, which is used to amplify the fasR gene.

<1-1> Coryneform Bacterium having L-Glutamic Acid Producing Ability

The coryneform bacterium of the present invention is able to produce L-glutamic acid, and has been modified so that expression of the fasR gene is enhanced. The coryneform bacterium also has improved sensitivity to a surfactant as compared to a bacterium in which the fasR gene is not enhanced.

The coryneform bacteria include *Corynebacterium* bacteria and those bacteria which were previously classified into the genus *Brevibacterium*, but have been re-classified into the genus *Corynebacterium* (Int. J. Syst. Bacteriol., 41, 255 (1981)), and further include bacteria belonging to the genus

*Brevibacterium*, which is extremely close to the genus *Corynebacterium*. Specific examples include the following:

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes (Corynebacterium efficiens)*
*Corynebacterium herculis*
*Brevibacterium divaricatum*
*Brevibacterium flavum*
*Brevibacterium immariophilum*
*Brevibacterium lactofermentum (Corynebacterium glutamicum)*
*Brevibacterium roseum*
*Brevibacterium saccharolyticum*
*Brevibacterium thiogenitalis*
*Brevibacterium ammoniagenes*
*Brevibacterium album*
*Brevibacterium cerinum*
*Microbacterium ammoniaphilum*

Specifically, the following strains can be mentioned:
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, ATCC 13032, ATCC 13060
*Corynebacterium lilium* ATCC 15990
*Corynebacterium melassecola* ATCC 17965
*Corynebacterium thermoaminogenes* AJ12340 (FERM BP-1539)
*Corynebacterium herculis* ATCC 13868
*Brevibacterium divaricatum* ATCC 14020
*Brevibacterium flavum* ATCC 13826, ATCC 14067
*Brevibacterium immariophilum* ATCC 14068
*Brevibacterium lactofermentum* ATCC 13869 (*Corynebacterium glutamicum* ATCC 13869)
*Brevibacterium roseum* ATCC 13825
*Brevibacterium saccharolyticum* ATCC 14066
*Brevibacterium thiogenitalis* ATCC 19240
*Brevibacterium ammoniagenes* ATCC 6871, ATCC 6872
*Brevibacterium album* ATCC 15111
*Brevibacterium cerinum* ATCC 15112
*Microbacterium ammoniaphilum* ATCC 15354

These strains are available from the American Type Culture Collection, and may be obtained by their designated registration number (www.atcc.org/). The registration number corresponding to each strain is listed in the catalogue of the ATCC. The AJ12340 strain was deposited at National Institute of Bioscience and Human Technology, Agency of Industrial Science and Technology, Ministry of International Trade and Industry (currently International Patent Organism Depositary, National Institute of Advanced Industrial Science and Technology at Tsukuba Central 6, 1-1, Higashi 1-chome, Tsukuba-shi, Ibaraki-ken 305-5466, Japan) on Oct. 27, 1987 under the provisions of the Budapest Treaty and given an accession number of FERM BP-1539.

In the present invention, "L-glutamic acid producing ability" or "able to produce L-glutamic acid" means that the bacteria have an ability to produce L-glutamic acid in a medium or cells when the coryneform bacterium is cultured in the medium. The bacteria may have a native ability to produce L-glutamic, or the ability may be imparted or enhanced by breeding. Furthermore, the L-glutamic acid producing ability may be imparted by enhancing expression of the fasR gene in the manner described herein.

To impart or enhance the ability to produce L-glutamic acid, the expression of a gene or genes encoding an enzyme or enzymes involved in L-glutamic acid biosynthesis may be increased or enhanced. Examples of these enzymes include glutamate dehydrogenase, glutamine synthetase, glutamate synthase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde-3-phophate dehydrogenase, triose phosphate isomerase, fructose bisphosphate aldolase, phosphofructokinase, glucose phosphate isomerase, and so forth.

To increase or enhance the expression of a gene or genes, a DNA fragment containing the desired gene or genes may be introduced into a suitable plasmid, for example, a plasmid vector containing at least a gene responsible for replication and proliferation of the plasmid, and the plasmid is then introduced into the coryneform bacteria. Another method for increasing expression of a gene or genes is by increasing the copy number of the gene or genes on the chromosome by conjugation, gene transfer etc., or by introducing a mutation into the promoter region of the gene or genes (refer to International Patent Publication WO95/34672). Examples of plasmids autonomously replicable in coryneform bacteria include, but are not limited to, pCRY30 (Japanese Patent Laid-open No. 3-210184), pCRY21, pCRY2KE, pCRY2KX, pCRY31, pCRY3KE, and pCRY3KX (Japanese Patent Laid-open No. 2-72876 and U.S. Pat. No. 5,185,262), pCRY2 and pCRY3 (Japanese Patent Laid-open No. 1-191686), pAM330 (Japanese Patent Laid-open No. 58-67679), pHM1519 (Japanese Patent Laid-open No. 58-77895), pAJ655, pAJ611, and pAJ1844 (Japanese Patent Laid-open No. 58-192900), pCG1 (Japanese Patent Laid-open No. 57-134500), pCG2 (Japanese Patent Laid-open No. 58-35197), pCG4 and pCG11 (Japanese Patent Laid-open No. 57-183799), and so forth.

When the desired gene or genes is/are introduced into the aforementioned plasmid or chromosome, any promoter may be used as long as the chosen promoter functions in coryneform bacteria. The promoter may either be the native promoter for the gene, or a modified promoter. Expression of the gene or genes can also be controlled by suitably choosing a promoter that is known to be strong in coryneform bacteria, or by approximating the −35 and −10 regions of promoter to the consensus sequence. Examples of coryneform bacteria with increased expression of the genes for citrate synthase, isocitrate dehydrogenase, pyruvate dehydrogenase, and/or glutamate dehydrogenase, are described in International Patent Publication WO00/18935, European Patent Publication No. 1010755, and so forth.

The ability to produce L-glutamic acid may also be induced by reducing or deleting the activity of an enzyme that catalyzes a reaction which causes the biosynthetic pathway of L-glutamic acid to branch off and produce a different compound. Examples of such enzymes include isocitrate lyase, α-ketoglutarate dehydrogenase, acetyl phosphate transferase, acetate kinase, acetohydroxy acid synthase, acetolactate synthase, acetyl formate transferase, lactate dehydrogenase, glutamate decarboxylase, 1-pyrroline dehydrogenase, and so forth. Examples of coryneform bacteria with decreased α-ketoglutarate dehydrogenase activity include the following:

*Brevibacterium lactofermentum* AS strain (WO95/34672)
*Brevibacterium lactofermentum* AJ12821 strain (FERM BP-4172; see FR9401748)
*Brevibacterium flavum* AJ12822 strain (FERM BP-4173; see FR9401748)
*Corynebacterium glutamicum* AJ12823 strain (FERM BP-4174; see FR9401748)

In order to reduce or delete activity of any one of the enzymes mentioned above, a mutation can be introduced by a known method into the gene which encodes the enzyme on the chromosome. For example, the gene encoding the enzyme can be deleted, or an expression control sequence such as a promoter and/or a Shine-Dalgarno (SD) sequence can be modified by gene recombination. Furthermore, a mutation which causes an amino acid substitution (missense mutation), a stop codon (nonsense mutation), or a frame shift mutation that adds or deletes one or two nucleotides in the gene can be introduced, or the gene may be partially or entirely deleted (Journal of Biological Chemistry, 272:8611-8617 (1997)). Other methods to reduce or delete the enzymatic activity include constructing a gene missing the coding region for the enzyme, and substituting the constructed gene for the normal gene on the chromosome by homologous recombination or the like, or by introducing a transposon or IS factor into the gene.

The following methods can be used to introduce such mutations into a gene. To replace the native gene on the chromosome with a mutant gene, a partial sequence of the objective gene can be modified, resulting in a mutant gene that does not produce a normal-functioning enzyme, and transforming a coryneform bacterium with a DNA containing the gene to cause recombination of the mutant gene and the native gene on the chromosome. Such site-specific mutagenesis based on gene substitution utilizing homologous recombination has been reported, and examples of methods include using a linear DNA or a plasmid containing a temperature sensitive replication origin (U.S. Pat. No. 6,303,383, Japanese Patent Laid-open No. 05-007491), and so forth. Moreover, site-specific mutagenesis based on gene substitution utilizing homologous recombination as described above can also be performed by using a plasmid which is not able to replicate in the chosen host.

Examples of temperature-sensitive plasmids for coryneform bacterium include p48K and pSFKT2 (U.S. Pat. No. 6,303,383), pHSC4 (French Patent Laid-open No. 2667875, 1992 and Japanese Patent Laid-open No. 5-7491), and so forth. These plasmids can autonomously replicate at a minimum of 25° C., but cannot autonomously replicate at 37° C. in coryneform bacteria. The *Escherichia coli* AJ12571 harboring pHSC4 was deposited at the National Institute of Bioscience and Human-Technology, the Agency of Industrial Science and Technology, the Ministry of International Trade and Industry (currently, the independent administrative corporation, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-5466)) on Oct. 11, 1990, receiving an accession number of FERM P-11763. Then, the deposit was converted to an international deposit under the provisions of the Budapest Treaty on Aug. 26, 1991, receiving an accession number of FERM BP-3524.

Other methods of imparting or enhancing the ability to produce L-glutamic acid include imparting resistance to organic acid analogs or respiratory inhibitors, or sensitivity to inhibitors of cell wall synthesis. Examples of such methods include, for example, imparting resistance to benzopirone or naphtoquinones (JP56-1889A), HOQNO (JP56-140895A), GL-ketomalonic acid (JP57-2689A), guanidine (JP56-35981A), daunomycin (JP58-158192A), and/or imparting sensitivity to penicillin (JP04-88994A), and so forth.

Specific examples of such resistant bacteria include the following:

*Brevibacterium flavum* AJ11355 (FERM P-5007; JP56-1889A)

*Corynebacterium glutamicum* AJ11368 (FERM P-5020; JP56-1889A)

*Brevibacterium flavum* AJ11217 (FERM P-4318; JP57-2689A)

*Corynebacterium glutamicum* AJ11218 (FERM P-4319; JP57-2689A)

*Brevibacterium flavum* AJ11564 (FERM P-5472; JP56-140895A)

*Brevibacterium flavum* AJ11439 (FERM P-5136; JP56-35981A)

*Corynebacterium glutamicum* H7684 (FERM BP-3004; JP04-88994A)

The coryneform bacterium which can be used to derive the coryneform bacterium of the present invention will produce L-glutamic acid even when the biotin concentration in the medium is restricted, or when the medium contains biotin at a high concentration and also includes a biotin suppressing agent, such as a surfactant or lactam antibiotic. Examples of the surfactant include saturated fatty acids such as lauric acid, myristic acid, stearic acid and palmitic acid, fatty acid ester type nonionic surfactants such as glycerol fatty acid esters, sorbitan fatty acid esters, sucrose fatty acid esters, polyethylene glycol fatty acid esters, polyethylene glycol/polypropylene glycol fatty acid esters and polyoxyethylene sorbitan fatty acid esters, and N-acylamino acids such as N-palmitoylglycine, N-palmitoylalanine, N-palmitoylvaline, N-palmitoylleucine, N-palmitoylthreonine, N-palmitoylmethionine, N-palmitoylaspartic acid, N-palmitoylglutamic acid, N-myristoylglutamic acid, N-stearoylglutamic acid, N,N'-dipalmitoylornithine and N,N'-dipalmitoyllysine. Examples of the antibiotic include lactam antibiotics such as penicillin and cephaloridine (Yamada K., Takahashi J. & Nakamura J., Hakkokogaku Kaishi, 20, 348-350 (1962), Udagawa K., Abe S. & Kinoshita S., Hakkokogaku Kaishi, 40, 614-619 (1962)).

Biotin concentration is considered to be restricted when the concentration in the medium is 30 µg/L or lower, preferably 20 µg/L or lower, more preferably 10 µg/L or lower, or the medium may not contain biotin at all. A high concentration of biotin means that the medium contains biotin at 50 µg/L or higher, preferably 100 µg/L or higher, more preferably 200 µg/L or higher. When the medium contains a high concentration of biotin, it will also contain a biotin suppressing agent, such as an antibiotic, at a concentration of 0.1 U/ml or higher, preferably 0.2 U/ml or higher, more preferably 0.4 U/ml or higher, or a surfactant at a concentration of 0.4 g/L or higher, preferably 1 g/L or higher, more preferably 2 g/L or higher. However, the concentrations may be at any level so long as L-glutamic acid production is induced.

Examples of strains which produce L-glutamic acid under the aforementioned conditions include, for example, wild-type strains of the coryneform bacteria and the following:

*Brevibacterium flavum* AJ11217 (FERM P-4318; JP57-2689A)

*Corynebacterium glutamicum* AJ11218 (FERM P-4319; JP57-2689A)

*Brevibacterium lactofermentum* AJ11426 (FERM P-5123 JP56-048890A)

*Corynebacterium glutamicum* AJ11440 (FERM P-5137 JP56-048890A)

*Brevibacterium lactofermentum* AJ11796 (FERM P-6402 JP58-158192A)

<1-2> Enhancement of fasR Gene Expression

Increased or enhanced expression of the fasR gene means that the number of FasR molecules per cell is increased as compared with that of the parent strain or a wild-type strain, or the activity of the FasR protein per molecule is increased, and so forth. The wild-type coryneform bacterium which can be used as a reference for comparison is, for example, *Corynebacterium glutamicum* (*Brevibacterium lactofermen-*

*tum*) ATCC13869 or ATCC13032. If the coryneform bacterium is modified so that expression of the fasR gene increases, sensitivity to a surfactant of the coryneform bacterium also increases.

In the present invention, the "activity which increases sensitivity to a surfactant" means the activity of the fasR gene product. Specifically, it means enabling L-glutamic acid production in a medium containing biotin at a high concentration by increasing the expression of the fasR gene. The "medium containing biotin at a high concentration" is a medium having a biotin concentration of 50 µg/L or higher, preferably 100 µg/L or higher, more preferably 200 µg/L or higher, and not containing a biotin suppressing agent such as penicillin or a surfactant, or containing the biotin suppressing agent at a reduced concentration. As for the biotin suppressing agent, a surfactant is desirably added at a concentration of 0.1 g/L or lower, preferably 0.05 g/L or lower, more preferably 0.01 g/L or lower, or it may not be added at all. Furthermore, when the parent strain is able to produce L-glutamic acid in a medium containing biotin at a high concentration and in the absence of a biotin suppressing agent, the ability to produce L-glutamic acid is improved as a result of the amplification of the fasR gene. The ability of the bacteria to produce L-glutamic acid in bacteria with increased expression of fasR is said to be improved if the strain with increased expression of the fasR gene produces L-glutamic acid in the medium or the rate at which the L-glutamic acid is produced is higher than that of a non-amplified strain. Also, it can be said that the L-glutamic acid producing ability is improved if the yield per saccharide is improved by increasing the expression of the fasR gene by, for example, 2% or more, desirably 4% or more, more desirably 6% or more, as compared with the parent strain or a non-modified strain.

An increase in fasR expression can be confirmed by comparing the amount of fasR mRNA with that of a wild-type or non-modified strain. Expression can be confirmed by conventional methods, including Northern hybridization and RT-PCR (Molecular Cloning, Cold Spring Harbor Laboratory Press, Cold Spring Harbor (USA) 2001). The degree to which expression is increased is not particularly limited so long as it is increased as compared with that of a wild strain or non-modified strain. However, it is increased, for example, 1.5 times or more, preferably 2 times or more, more preferably 3 times or more, as compared with a wild-type strain or non-modified strain.

The protein encoded by the fasR gene is a kind of transcriptional regulator, or a homologue thereof, and has an activity of improving sensitivity of coryneform bacteria to a surfactant when expression of the gene is enhanced (Fatty Acid Synthase Regulator, fasR). Examples of the gene encoding fasR (fasR gene) of coryneform bacteria include, for example, DNA having at least the nucleotides 506 to 976 of SEQ ID NO: 3 derived from *C. glutamicum* (*B. lactofermentum*) ATCC 13869, and a gene having the nucleotide sequence of SEQ ID NO: 5 derived from *C. glutamicum* ATCC 13032. The fasR gene of *Corynebacterium glutamicum* ATCC 13032 is encoded by the nucleotides 3189878 to 3190351 in the genome sequence registered as Genbank Accession No. NC_003450, and also is registered as NCgl 2886. Moreover, homologous genes to fasR derived from other microorganisms may also be used so long as sensitivity to a surfactant can be enhanced by amplification of the gene in coryneform bacteria. Homologues of the fasR gene can be found by searching with reference to the gene sequence of NCgI 2886 by using BLAST or the like (blast.genome.jp/).

Since the sequence of the fasR gene has already been elucidated, fasR and a flanking region thereof including the control region of fasR can be obtained by PCR (polymerase chain reaction, see White, T. J. et al., Trends Genet., 5, 185 (1989)) using primers prepared on the basis of the elucidated nucleotide sequence, for example, the primers shown in SEQ ID NOS: 1 and 2 and chromosomal DNA of a coryneform bacterium as a template. Homologues of fasR of other microorganisms can also be obtained in a similar manner.

Moreover, since the nucleotide sequence of the fasR gene may differ among the various species or strains of coryneform bacteria, the fasR gene to be used for the present invention is not limited to the nucleotide sequence 506 to 967 of SEQ ID NO: 3 or that of SEQ ID NO: 5, and may include mutants and/or artificially modified sequences encoding a protein having the amino acid sequence of SEQ ID NO: 4 or 6. The encoded protein sequences may include substitutions, deletions, insertions, additions, or inversions of one or several amino acid residues at one or more positions, so long as the function of the encoded FasR protein is maintained, namely, it can improve the sensitivity to surfactant by amplification thereof. Although the number of amino acid residues referred to herein may differ depending on their relative position in the three-dimensional structure or the types of amino acid residues, it may be preferably 1 to 20, more preferably 1 to 10, particularly preferably 1 to 5. Moreover, such substitution, deletion, insertion, addition, and inversion of amino acid residues as mentioned above include those alterations caused by a naturally occurring mutation or variation based on the difference in individuals or species of the microorganisms containing the fasR gene.

The aforementioned substitution is preferably a conservative substitution which is a neutral mutation not causing a functional change. Conservative substitutions include: substitutions of the aromatic amino acids Phe, Trp, and Tyr for each other, substitutions of the hydrophobic amino acids Leu, Ile, and Val for each other, substitutions of polar amino acids Gln and Asn for each other, substitutions of the basic amino acids Lys, Arg, and His for each other, substitutions of the acidic amino acids Asp and Glu for each other, and substitutions of the hydroxyl group-containing amino acids Ser and Thr. More specifically, examples of the conservative mutations include: substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr and substitution of Met, Ile, or Leu for Val.

Furthermore, a gene encoding a protein having a homology of 80% or more, preferably 90% or more, more preferably 95% or more, particularly preferably 97% or more, to the entire amino acid sequence of SEQ ID NO: 4 or 6 may be used, and also is capable of improving sensitivity to a surfactant of coryneform bacteria by enhancing the expression of this gene. Moreover, since the gene may have alterations in the sequence depending on the host due to the degeneracy of the genetic code, codons in the fasR gene may be replaced with codons that are amenable to the chosen host. The fasR gene may also be extended or deleted so as to extend or delete the protein on the N-terminus side or the C-terminus side, so long as it is able to improve sensitivity of coryneform bacteria to a surfactant when amplified. The length of the extension or deletion is, for example, 50 amino acids or less, preferably 20 or less, more preferably 10 or less, particularly preferably 5 or less. More specifically, it may be a protein having between 5 and 50 amino acids deleted from either the N-terminus or C-terminus side of the amino acid sequence of SEQ ID NO: 4, or a protein having between 5 and 50 amino acids added to either end of the amino acid sequence of SEQ ID NO: 4.

Genes homologous to the fasR gene can be obtained by, for example, modifying the nucleotide sequence of 506 to 976 of SEQ ID NO: 3 or the nucleotide sequence of SEQ ID NO: 5, by site-specific mutagenesis so that amino acids at specific sites of the encoded protein are substituted, deleted, inserted, or added. Furthermore, conventionally known mutagenesis treatments may also be used, such as treating the nucleotide sequence of 506 to 976 of SEQ ID NO: 3 or the nucleotide sequence of SEQ ID NO: 5 with hydroxylamine, or the like, in vitro, treating a microorganism such as a coryneform bacterium containing the gene with ultraviolet radiation or a commonly-used mutagenesis agent, such as N-methyl-N'-nitro-N-nitrosoguanidine (NTG) or ethyl methanesulfonate (EMS). A mutation can be artificially introduced into fasR by gene recombination to obtain a highly active fasR by error-prone PCR, DNA shuffling, or StEP-PCR (Firth A E, Patrick W M, Bioinformatics., 2005 Jun. 2, Statistics of protein library construction). Whether the fasR homologous gene encodes a protein that improves sensitivity to a surfactant when expression of the gene is increased can be confirmed by, for example, introducing the gene into a wild-type strain of a coryneform bacterium, and examining whether the L-glutamic acid producing ability is improved in a medium with no surfactant.

The fasR gene also includes a DNA which is able to hybridize with the nucleotide sequence of 506 to 976 of SEQ ID NO: 3, the nucleotide sequences of SEQ ID NO: 5, or a probe which can be prepared from the foregoing sequences under stringent conditions and encoding a protein which improves sensitivity to a surfactant of coryneform bacteria when expression of the gene is enhanced. Here, the "stringent conditions" are conditions under which a so-called specific hybrid is formed, and a non-specific hybrid is not formed. Examples of the stringent conditions include those under which highly homologous DNAs hybridize to each other, for example, DNAs not less than 80, 90, 95, or 97% homologous, hybridize to each other, and DNAs less homologous than the above do not hybridize to each other, or conditions of washing once or preferably 2 or 3 times at a salt concentration and temperature corresponding to washing conditions in typical Southern hybridization, i.e., 1×SSC, 0.1% SDS at 60° C., preferably 0.1×SSC, 0.1% SDS at 60° C., more preferably 0.1×SSC, 0.1% SDS at 68° C.

A probe having a partial sequence of the nucleotide sequence of 506 to 976 of SEQ ID NO: 3 or the nucleotide sequences of SEQ ID NO: 5 can also be used. Such a probe can be produced by PCR using oligonucleotides prepared on the basis of the nucleotide sequence of 506 to 976 of SEQ ID NO: 3 or the nucleotide sequences of SEQ ID NO: 5 as primers, and a DNA fragment containing the nucleotide sequence of 506 to 976 of SEQ ID NO: 3 or the nucleotide sequences of SEQ ID NO: 5 as a template. When a DNA fragment of about 300 bp is used as the probe, the washing conditions of hybridization are, for example, 2×SSC, 0.1% SDS at 50° C.

Increasing or enhancing expression of the fasR gene can be attained by increasing the copy number of the fasR gene. For example, a recombinant DNA can be prepared by ligating a gene fragment containing the fasR gene with a vector able to function in coryneform bacteria, preferably such a multi-copy type vector, and transforming a host having the aforementioned L-glutamic acid producing ability with the vector. Alternatively, the aforementioned recombinant DNA can be introduced into a wild-type coryneform bacterium, and then the ability to produce L-glutamic acid can be imparted to the transformant. The copy number can also be increased by transferring one or more copies of a gene encoding fasR to the chromosome, which can be confirmed by Southern hybridization using a portion of the fasR gene as a probe.

Expression of the fasR gene can also be increased or enhanced by modifying an expression control sequence of the fasR gene, for example, by replacing a promoter sequence of the fasR gene with a stronger promoter, or approximating a promoter sequence to a consensus sequence (International Patent Publication WO00/18935).

Methods for constructing a coryneform bacterium which is modified so that expression of the fasR gene is increased are shown below. These methods can be performed by referring to manuals such as Molecular Cloning (Cold Spring Harbor Laboratory Press, Cold Spring Harbor (USA), 2001).

Expression of the fasR gene can be increased by increasing the copy number of the gene, for example, by amplifying the fasR gene using a plasmid as described below. First, the fasR gene is cloned from the chromosome of a coryneform bacterium. Chromosomal DNA can be prepared from the bacterium by, for example, the method of Saito and Miura (refer to H. Saito and K. Miura, Biochem. Biophys. Acta, 72, 619 (1963); Text for Bioengineering Experiments, Edited by the Society for Bioscience and Bioengineering, Japan, pp. 97-98, Baifukan, 1992), or the like. Oligonucleotides useful in PCR can be synthesized on the basis of known information such as mentioned above, and the fasR gene can be amplified by using, for example, the synthetic oligonucleotides of SEQ ID NOS: 1 and 2.

If a PCR-amplified gene fragment containing the fasR gene is ligated to a vector DNA which is able to autonomously replicate in *Escherichia coli* and/or coryneform bacteria, and then introduced into *Escherichia coli*, the subsequent procedure becomes routine. Examples of vectors able to autonomously replicate in *Escherichia coli* include pUC19, pUC18, pHSG299, pHSG399, pHSG398, RSF110, pBR322, pACYC184, pMW219, and so forth.

The aforementioned DNA is introduced into a vector which is able to function in coryneform bacteria, such as, for example, a plasmid that can autonomously replicate in coryneform bacteria. Specific examples include, for example, pCRY30 (Japanese Patent Laid-open No. 3-210184), pCRY21, pCRY2KE, pCRY2KX, pCRY31, pCRY3KE, and pCRY3KX (Japanese Patent Laid-open No. 2-72876 and U.S. Pat. No. 5,185,262), pCRY2 and pCRY3 (Japanese Patent Laid-open No. 1-191686), pAM330 (Japanese Patent Laid-open No. 58-67679), pHM1519 (Japanese Patent Laid-open No. 58-77895), pAJ655, pAJ611 and pAJ1844 (Japanese Patent Laid-open No. 58-192900), pCG1 (Japanese Patent Laid-open No. 57-134500), pCG2 (Japanese Patent Laid-open No. 58-35197), pCG4 and pCG11 (Japanese Patent Laid-open No. 57-183799), and pVK7 (Japanese Patent Laid-open No. 10-215883).

Moreover, if a DNA fragment which is able to induce to a plasmid the ability to autonomously replicate in coryneform bacteria is inserted into the aforementioned vectors for *Escherichia coli*, they can be used as a so-called shuttle vector which is autonomously replicable in both *Escherichia coli* and coryneform bacteria.

These vectors can be obtained from the deposited bacteria as follows. That is, cells collected in their exponential growth phase are lysed with lysozyme and SDS, and centrifuged at 30000×g. Polyethylene glycol is added to the supernatant obtained from the lysate, fractionated, and purified by cesium chloride-ethidium bromide equilibrium density gradient centrifugation.

In order to ligate the fasR gene to a vector that functions in coryneform bacteria, the vector is digested with a restriction enzyme which results in the matching end for the fasR gene.

This restriction site may be previously introduced into the synthetic oligonucleotides used for the amplification of the fasR gene. The ligation is usually performed by using a ligase such as T4 DNA ligase.

Known transformation methods that have previously been reported can be used to introduce the recombinant DNA prepared as described above into a coryneform bacterium. For instance, treating recipient cells with calcium chloride so as to increase permeability of the cells for DNA, which has been reported for *Escherichia coli* K-12 (Mandel, M. and Higa, A., J. Mol. Biol., 53, 159 (1970)), and preparing competent cells from cells which are at the growth phase followed by transforming with the DNA, which has been reported for *Bacillus subtilis* (Duncan, C. H., Wilson, G. A. and Young, F. E., Gene, 1, 153 (1977)) may be used. In addition, other methods include making DNA-recipient cells into protoplasts or spheroplasts which can easily take up recombinant DNA, followed by transforming with the recombinant DNA, which is known to be applicable to *Bacillus subtilis*, actinomycetes and yeasts (Chang, S, and Choen, S. N., Mol. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci. USA, 75, 1929 (1978)). In addition, coryneform bacteria can also be transformed by the electric pulse method (Japanese Patent Laid-open No. 2-207791) or conjugative transfer (Biotechnology (N Y), 1991 January, 9(1):84-7).

The copy number of the fasR gene can also be increased by introducing multiple copies of the fasR gene into a chromosomal DNA of coryneform bacteria via homologous recombination using a sequence present in multiple copies on the chromosomal DNA as a target. Sequences present in multiple copies on the chromosomal DNA include repetitive DNA, and inverted repeats present at the end of a transposable element. Alternatively, as disclosed in Japanese Patent Laid-open No. 2-109985, the fasR gene may be incorporated into a transposon, and transferred to introduce multiple copies of the gene into the chromosomal DNA (Japanese Patent Laid-open Nos. 2-109985 and 7-107976; Mol. Gen. Genet., 245, 397-405 (1994); Plasmid, 2000 November, 44(3):285-91).

Moreover, the fasR gene may be introduced into a plasmid which contains a replication origin unable to replicate in the chosen host, or, in addition is capable of conjugative transfer to the host, thereby amplifying the gene on the chromosome. Examples of usable vectors include, for example, pSUP301 (Simo et al., Bio/Technology, 1, 784-791 (1983)), pK18mob, or pK19mob (Schaefer et al., Gene, 145, 69-73 (1994)), pGEM-T (Promega, Madison, Wis., USA), pCR2.1-TOPO (Shuman, Journal of Biological Chemistry, 269: 32678-84 (1994); U.S. Pat. No. 5,487,993), pCR® Blunt (Invitrogen, Groningen, Netherlands; Bernard et al., Journal of Molecular Biology, 234:534-541 (1993)), pEM1 (Schrumpf et al., Journal of Bacteriology, 173: 1991, 4510-4516), pBGS8 (Spratt et al, 1986, Gene, 41:337-342), and so forth. A plasmid vector containing the fasR gene is then transferred into a coryneform bacterium by conjugation or transformation. Methods for conjugation are described in, for example, Schaefer et al. (Applied and Environmental Microbiology, 60, 756-759 (1994)). Methods for transformation are described in, for example, Theirbach et al., Applied Microbiology and Biotechnology, 29, 356-362 (1988); Dunican and Shivinan, Bio/Technology 7, 1067-1070, (1989); and Tauch et al., FEMS Microbiological Letters, 123, 343-347 (1994).

Moreover, the activity of the fasR protein can also be increased by replacing an expression control sequence, such as a promoter, on the chromosomal DNA or in a plasmid with a stronger promoter, modifying a factor which controls expression of the fasR gene, for example, an operator or a repressor, or ligating a potent terminator (Hamilton et al, Journal of Bacteriology, 171:4617-4622). For example, the lac promoter, trp promoter, trc promoter, PS2 promoter, and so forth are known as strong promoters. Methods for evaluating the potency of promoters and examples of potent promoters are described in Goldstein et al. (Prokaryotic promoters in biotechnology, Biotechnol. Annu. Rev., 1995, 1, 105-128), and so forth. Moreover, as disclosed in International Patent Publication WO00/18935, one or more nucleotide substitutions may be introduced into the promoter region of the objective gene so as to convert the promoter sequence into a consensus sequence, and thereby making it stronger. For example, the TTGACA or TTGCCA sequence may be substituted for the −35 region, or the TATAAT or TATAAC sequence may be substituted for the −10 region. Furthermore, it is known that by replacing several nucleotides in the spacer region between the ribosome binding site (RBS) and the start codon, particularly in the region immediately upstream from the start codon, the translation efficiency of mRNA can be significantly affected. In addition, these regions can also be modified.

Furthermore, expression can also be increased by extending the lifetime of the mRNA, or by preventing decomposition of enzyme proteins in cells. Expression control regions of the fasR gene, such as the promoter in the upstream region, can also be determined by using a promoter searching vector, gene analysis software such as GENETYX, or the like. By such promoter substitution or modification, expression of the fasR gene is enhanced. Substitution of an expression control sequence can be performed by using, for example, a temperature-sensitive plasmid, such as p48K and pSFKT2 (Japanese Patent Laid-open No. 2000-262288), pHSC4 (French Patent Laid-open No. 2667875, 1992 and Japanese Patent Laid-open No. 5-7491), and so forth, for coryneform bacteria. These plasmids can autonomously replicate at a minimum of 25° C., but cannot autonomously replicate at 37° C. in coryneform bacteria. The expression control sequence may be modified in combination with increasing the copy number of the fasR gene.

<2> Production of L-Glutamic Acid

L-glutamic acid can be efficiently produced by culturing a coryneform bacterium obtained as described above in a medium to produce and cause accumulation of L-glutamic acid in the medium and collecting L-glutamic acid from the medium.

Any ordinary medium that contains a carbon source, a nitrogen source, an inorganic salt, and optionally organic micronutrients such as amino acids and vitamins can be used. Either a synthetic or a natural medium may be used. Any kind of carbon and nitrogen sources may be used so long as they can be utilized by the strain being cultured.

Saccharides such as glucose, glycerol, fructose, sucrose, maltose, mannose, galactose, starch hydrolysate, molasses, and so forth may be used as the carbon source. In addition, organic acids such as acetic acid and citric acid, and alcohols such as ethanol may also be used alone or in combination with other carbon sources. Ammonia, ammonium salts such as ammonium sulfate, ammonium carbonate, ammonium chloride, ammonium phosphate, and ammonium acetate, nitrates, and so forth may be used as the nitrogen source. Amino acids, vitamins, fatty acids, nucleic acids, and peptone, casamino acid, yeast extract, and soybean protein decomposition products which contain these substances may be used as the organic micronutrients. When using an auxotrophic mutant strain that requires an amino acid etc. for growth, the required nutrients are preferably added. Phosphates, magnesium salts, calcium salts, iron salts, manganese salts, and so forth can be used as inorganic salts.

In the case of the present invention, since the amount of surfactant required for induction of L-glutamic acid production can be reduced by amplifying the fasR gene, the medium may contain biotin at a high concentration. The medium desirably contains biotin at a concentration is 50 μg/L or higher, preferably 100 μg/L or higher, more preferably 200 μg/L or higher.

Aerobic culturing is performed by controlling the fermentation temperature to 20 to 45° C. and adjusting the pH of the culture medium to 3 to 9. When the pH decreases during the culture, the medium is neutralized by adding alkali such as calcium carbonate or ammonia gas. Culture for about 10 to about 120 hours results in accumulation of a marked amount of L-glutamic acid in the medium.

Furthermore, the culture can also be performed by precipitating L-glutamic acid into the medium by using a liquid medium adjusted to precipitate L-glutamic acid. L-glutamic acid typically precipitates at pH 5.0 to 4.0, preferably pH 4.5 to 4.0, more preferably pH 4.3 to 4.0, particularly preferably pH 4.0.

Known collection methods may be used to collect L-glutamic acid from the medium after the culture. For example, such methods include removing cells from the medium, and causing crystallization by concentration, ion exchange chromatography, or the like. When the culture is performed under conditions which cause precipitation of L-glutamic acid, the precipitated L-glutamic acid can be collected by centrifugation or filtration. In this case, L-glutamic acid which has dissolved in the medium may be precipitated and then separated together.

EXAMPLES

The present invention will be specifically explained with reference to the following non-limiting examples.

Example 1

Preparation of a fasR-Amplified Strain of *C. glutamicum* ATCC13869

A plasmid for amplifying the fasR gene was prepared. Since the total genome sequence of *C. glutamicum* has been reported, a chromosome was extracted from *C. glutamicum* ATCC13869 by using Bacterial Genomic DNA Purif. Kit (MS Techno Systems), and PCR was performed using this chromosome as a template and a combination of the primers of SEQ ID NOS: 1 and 2 to amplify a fragment of about 900 bp. PCR was performed by using Pyrobest polymerase (Takara Bio Inc.) with a cycle of denaturation at 98° C. for 10 seconds, annealing at 55° C. for 30 seconds, and extension at 72° C. for 2 minutes, which was repeated 25 times. The KpnI sequence was added to the primers of SEQ ID NOS: 1 and 2 at the 5'-end, and the region of 111 to 1010 of SEQ ID NO: 3 was amplified.

The amplified fragment was completely digested with KpnI, and ligated to the pVK7 vector (described in Japanese Patent Laid-open No. 10-215883) which had been similarly completely digested with KpnI (Ligation Kit Ver. 2 (Takara Bio Inc.) was used) to construct pVKFASR (the construction scheme is shown in FIG. 1).

pVKFASR was introduced into *C. glutamicum* ATCC13869 by the electric pulse method (Japanese Patent Laid-open No. 2-207791), and the cells were applied to the CM-2B agar medium (10 μl of polypeptone, 5 μl of yeast extract, 5 μl of NaCl, 10 μl of biotin, 20 g/l of agar, adjusted to pH 7.0 with KOH) containing 25 μg/ml of kanamycin. The strain that appeared was designated ATCC13869/pVKFASR as a fasR-amplified strain.

Example 2

Confirmation of Glutamic Acid Producing Ability of ATCC 13869/pVKFASR Strain

The ability of the ATCC13869/pVKFASR strain to produce glutamic acid was examined by performing the culture using a Sakaguchi flask. A control strain, ATCC13869/pVK7, which was obtained by introducing the vector into the wild-type strain, and the fasR-amplified ATCC13869/pVKFASR strain were cultured at 31.5° C. in the CM-2B agar medium (10 μl of polypeptone, 5 μl of yeast extract, 5 μl of NaCl, 10 μg/l of biotin, 20 μl of agar, adjusted to pH 7.0 with KOH) containing 25 μg/ml of kanamycin for one whole day, and inoculated into 20 ml of a seed culture medium (80 μl of glucose, 30 μl of ammonium sulfate, 1 μl of $KH_2PO_4$, 0.4 g/l of $MgSO_4.7H_2O$, 0.01 μl of $FeSO_4.7H_2O$, 0.01 μl of $MnSO_4.4$-$5H_2O$, 200 μg/l of vitamin B1, 0.48 μl of soy bean protein hydrolysate, 300 μl of biotin, adjusted to pH 8.0 with KOH). One g of calcium carbonate which had been previously subjected to dry heat sterilization was added to the medium, and then cultured at 31.5° C. with shaking at a velocity of 115 rpm. After confirming that the total sugar was completely consumed, 1 ml of the seed culture medium was inoculated into 20 ml of the main culture medium (80 μl of glucose, 30 μl of ammonium sulfate, 1 μl of $KH_2PO_4$, 0.4 g/l of $MgSO_4.7H_2O$, 0.01 μl of $FeSO_4.7H_2O$, 0.01 g/l of $MnSO_4.4$-$5H_2O$, 200 μg/l of vitamin B1, 0.48 μl of soy bean protein hydrolysate, 300 μl of biotin, adjusted to pH 8.0 with KOH). One g of calcium carbonate which had been previously subjected to dry heat sterilization was added to the medium, and then cultured at 31.5° C. with shaking at a velocity of 115 rpm. After 2.5 hours from the start of the culture, 0.01, 0.1, or 1 g/l of Tween 40 (Sigma) was added, or Tween 40 was not added. The cell amounts (absorption was measured at 620 nm), the amount of accumulated glutamic acid, and the amount of remaining saccharide after 41 hours are shown in Table 1.

As a result, the ATCC13869/pVKFASR strain produced about 10 μl of glutamic acid when surfactant was not added or added in a small amount, whereas the ATCC13869/pVK7 strain did not produce glutamic acid. From the above results, it was confirmed that amplification of the fasR gene was effective for completely eliminating the need of a surfactant or reducing the amount of surfactant, which is usually necessary for induction of glutamic acid production.

TABLE 1

Glutamic acid production amounts of *fasR*-amplified strain

| Concentration of surfactant | Strain | OD620 nm | Glutamic acid (g/l) | Remaining saccharide (g/l) |
|---|---|---|---|---|
| 0 g/l | ATCC13869/pVK7 | 80.68 | 0.0 | 0.0 |
| | ATCC13869/pVKFASR | 64.41 | 11.0 | 0.0 |

TABLE 1-continued

Glutamic acid production amounts of fasR-amplified strain

| Concentration of surfactant | Strain | OD620 nm | Glutamic acid (g/l) | Remaining saccharide (g/l) |
|---|---|---|---|---|
| 0.01 g/l | ATCC13869/pVK7 | 79.15 | 0.0 | 0.0 |
| | ATCC13869/pVKFASR | 66.05 | 6.8 | 0.0 |
| 0.1 g/l | ATCC13869/pVK7 | 78.49 | 0.0 | 0.0 |
| | ATCC13869/pVKFASR | 60.59 | 11.8 | 0.0 |

Example 3

Change of Sensitivity of ATCC13869/pVKFASR Strain to Surfactant

Figure 2:
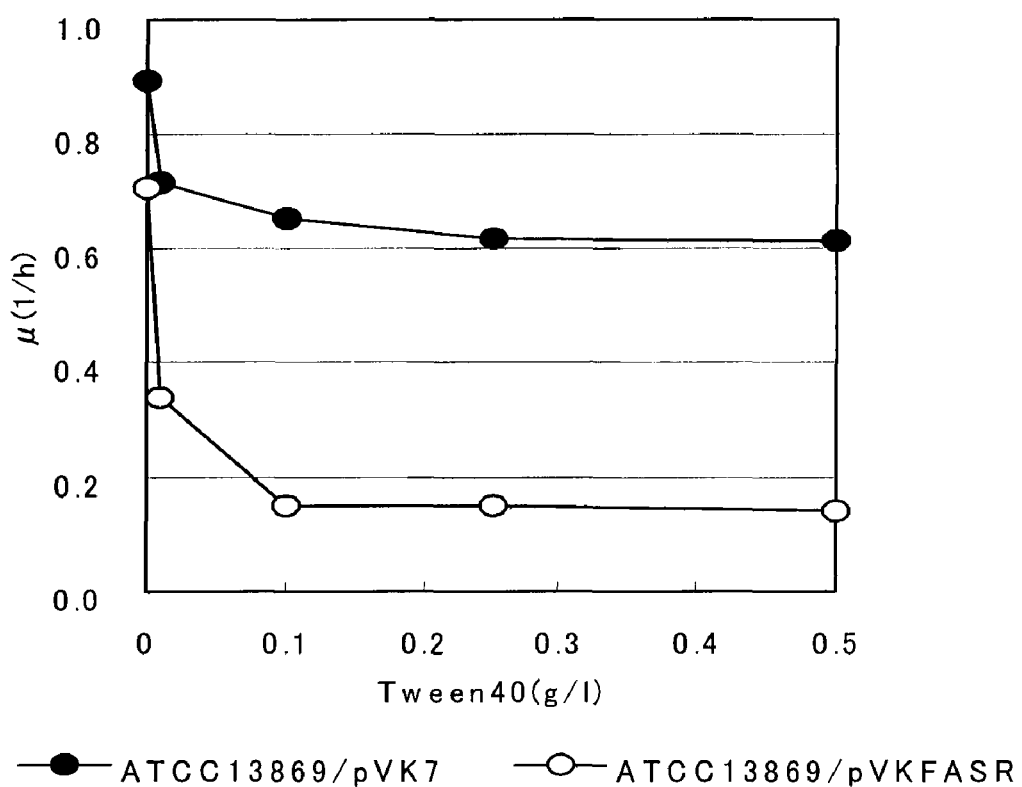
FIG. 2 shows a graph showing the growth curve of the fasR gene-amplified strain in the presence of a surfactant.

Since glutamic acid production was induced in the fasR-amplified strain only at low concentrations of surfactant, it appears that the sensitivity of the strain to the surfactant increased as compared with the control strain (vector-introduced strain ATCC13869/pVK7). Therefore, the sensitivity of the fasR-amplified strain to a surfactant was examined. Cells grown at 31.5° C. on the CM-2B agar medium over one whole day were inoculated to the CM-2B liquid medium, and Tween 40 was added to the medium at a concentration of 0.01, 0.1, 0.25 or 0.5 µl, or was not added. By performing a test tube culture, absorption at 620 nm (OD 620 nm) was measured over time. The specific growth rate was calculated, and the results are shown in FIG. 2. A marked decrease in the specific growth rate was observed for the fasR-amplified strain when 0.01 g/L of the surfactant was added, and thus it was confirmed that the fasR gene was able to change the sensitivity to a surfactant.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

The invention claimed is:

1. A method for producing L-glutamic acid comprising:
   A) culturing a coryneform bacterium in a medium, and
   B) collecting L-glutamic acid from the medium,
   wherein said coryneform bacterium is modified so that the expression of the fasR gene is enhanced as compared to a parent strain by increasing the copy number of the gene or modifying an expression control sequence of the gene,
   wherein said bacterium is able to produce L-glutamic acid in a medium containing 50 μg/l or more biotin without adding a biotin activity suppressing agent selected from the group consisting of a surfactant and penicillin, and wherein the fasR gene is selected from the group consisting of:
   a) a DNA comprising nucleotides 506 to 976 in SEQ ID NO: 3 or nucleotides 1 to 474 in SEQ ID NO: 5,
   b) a DNA which is able to hybridize with nucleotides 506 to 976 in SEQ ID NO: 3, or nucleotides 1 to 474 in SEQ ID NO: 5, under stringent conditions comprising washing at 0.1×SSC, 0.1% SDS at 60° C.

2. The method according to claim 1, wherein said bacterium is *Corynebacterium glutamicum*.

3. The method according to claim 1, wherein said fasR gene has a homology of 95% or more to the entire amino acid sequence of SEQ ID NO: 4 or SEQ ID NO: 6.

* * * * *